United States Patent [19]

Dessau

[11] Patent Number: 5,122,489

[45] Date of Patent: Jun. 16, 1992

[54] NON-ACIDIC DEHYDROGENATION CATALYST OF ENHANCED STABILITY

[75] Inventor: Ralph M. Dessau, Edison, N.J.

[73] Assignee: Mobil Oil Corporation, Fairfax, Va.

[21] Appl. No.: 597,124

[22] Filed: Oct. 15, 1990

[51] Int. Cl.⁵ ............................................. B01J 29/32
[52] U.S. Cl. ........................................ 502/66; 502/74
[58] Field of Search ................................... 502/66, 74

[56] References Cited

U.S. PATENT DOCUMENTS

| | | | |
|---|---|---|---|
| Re. 29,948 | 3/1979 | Dwyer et al. | 208/110 |
| 3,523,914 | 8/1970 | Mitsche et al. | 502/66 |
| 3,702,293 | 11/1972 | Hayes et al. | 208/139 |
| 3,702,294 | 11/1972 | Rausch | 208/139 |
| 3,878,131 | 4/1974 | Hayes | 252/466 PT |
| 4,104,320 | 8/1978 | Bernard et al. | 260/673.5 |
| 4,325,808 | 4/1982 | Kim et al. | 208/65 |
| 4,347,394 | 8/1982 | Detz et al. | 585/419 |
| 4,387,258 | 6/1983 | Vadekar et al. | 585/259 |
| 4,416,806 | 11/1983 | Bernard et al. | 502/74 |
| 4,418,006 | 11/1983 | Kim et al. | 502/73 |
| 4,435,283 | 3/1984 | Buss et al. | 208/138 |
| 4,456,527 | 6/1984 | Buss et al. | 208/89 |
| 4,486,547 | 12/1984 | Imai et al. | 502/223 |
| 4,487,843 | 12/1984 | Telford et al. | 502/85 |
| 4,487,848 | 12/1984 | Robinson et al. | 502/223 |
| 4,544,645 | 10/1985 | Klaassen et al. | 502/66 |
| 4,547,472 | 10/1985 | Nordstrand | 502/66 |
| 4,576,805 | 3/1986 | Chang et al. | 423/277 |
| 4,588,495 | 5/1986 | Franck et al. | 208/65 |
| 4,604,371 | 8/1986 | Moorehead | 502/60 |
| 4,614,834 | 9/1986 | Lambert et al. | 585/419 |
| 4,619,906 | 10/1986 | Lambert et al. | 502/166 |
| 4,868,145 | 9/1989 | Dessau et al. | 502/68 |
| 4,931,416 | 6/1990 | Dessau et al. | 502/66 |
| 4,982,028 | 1/1991 | Dessau et al. | 585/277 |

FOREIGN PATENT DOCUMENTS

| | | |
|---|---|---|
| 74651 | 9/1982 | European Pat. Off. . |
| 0107389 | 4/1984 | European Pat. Off. . |
| 256513 | 5/1988 | Fed. Rep. of Germany ........ 502/66 |
| 2520636 | 1/1983 | France . |
| 2033358 | 5/1980 | United Kingdom . |
| 2114150 | 8/1983 | United Kingdom . |
| 8904818 | 6/1989 | World Int. Prop. O. ............ 502/66 |

OTHER PUBLICATIONS

Huagong, vol. 15, No. 7 (1986) (with translation).
G. Wengui et al., "IR Study of Framework Vibrations and Surface Properties High Silica Zeolites", Zeolites, Elsevir Science, Amsterdam, 1985, p. 27.
Ione, Journal of Molecular Catalysis, 31, pp. 355-370 (1985).
Ione, "Structure and Reactivity of Modified Zeolites", Elsevir Science (1984), pp. 151-155.

*Primary Examiner*—Carl F. Dees
*Attorney, Agent, or Firm*—Alexander J. McKillop; Charles J. Speciale; Marina V. Schneller

[57] ABSTRACT

A metal selected from the group consisting of ruthenium, iridium or rhenium on non-acidic microporous crystalline materials also containing a dehydrogenation/hydrogenation metal enhances the aging characteristics and stability of the base catalyst.

16 Claims, 1 Drawing Sheet

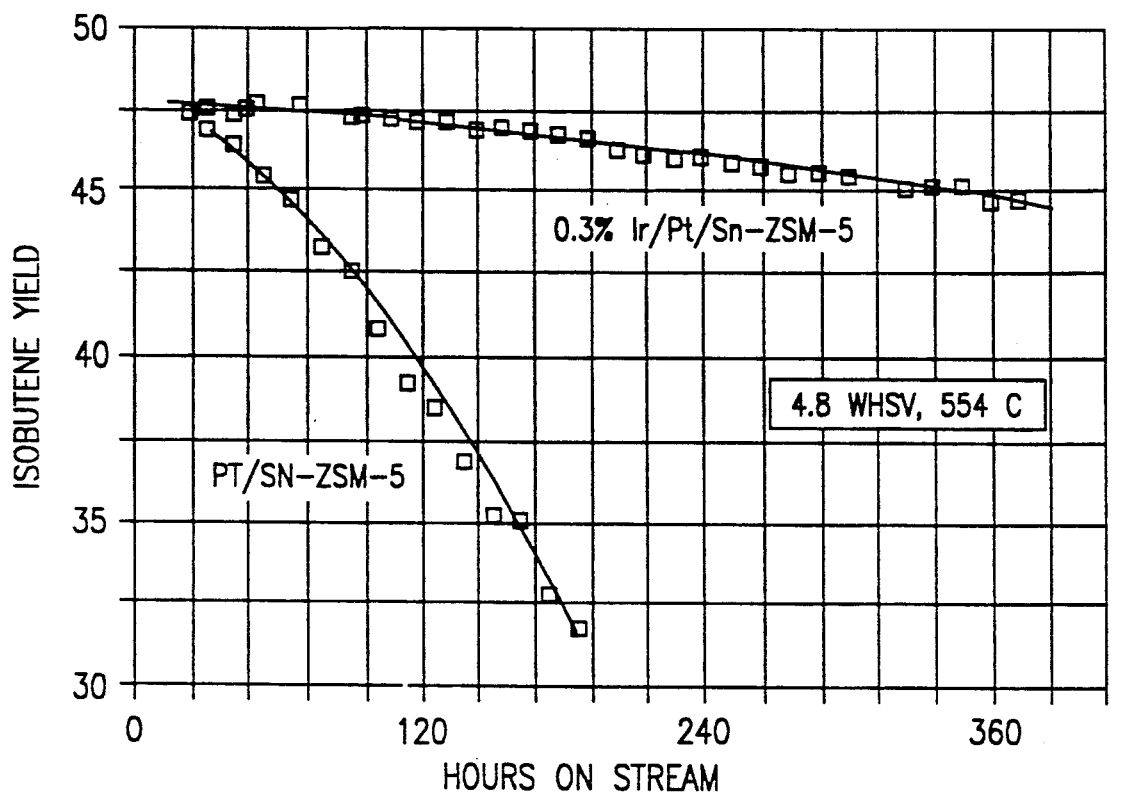
FIG. 1  EFFECT OF IRIDIUM ADDITION
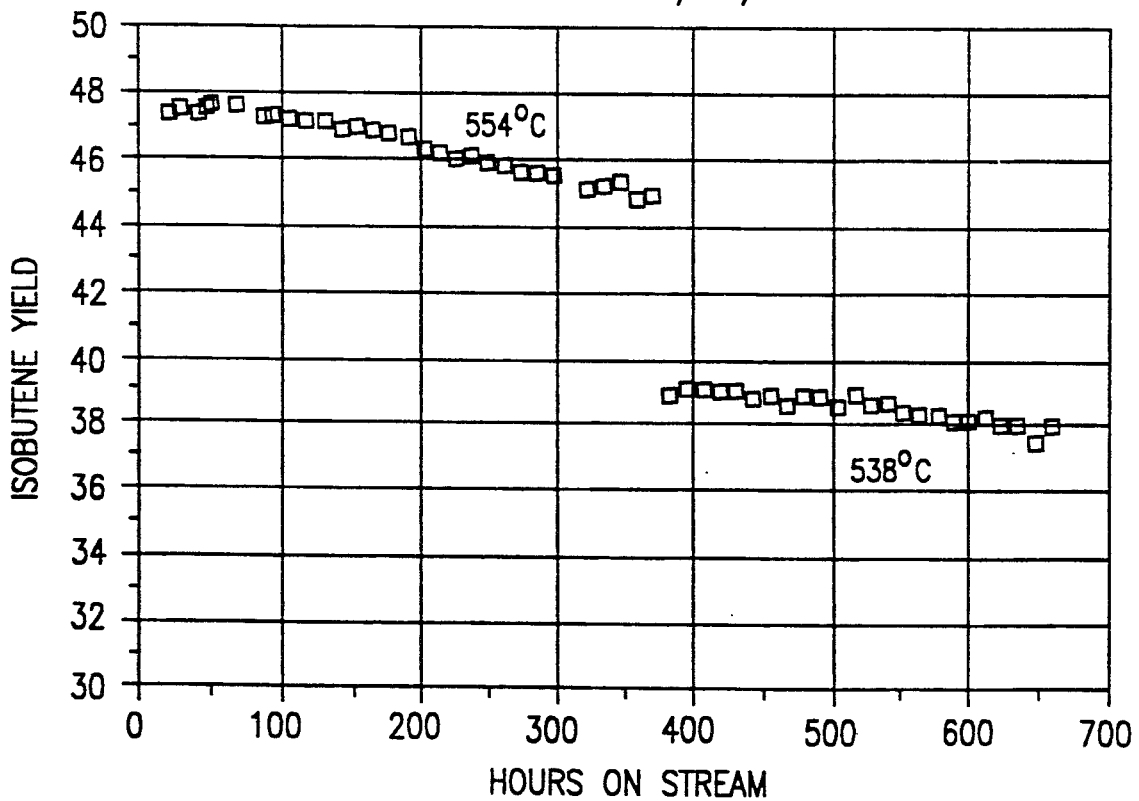
FIG. 2  AGING BEHAVIOR OF IR/PT/SN-ZSM-5

NON-ACIDIC DEHYDROGENATION CATALYST OF ENHANCED STABILITY

FIELD OF THE INVENTION

Dehydrogenation/hydrogenation catalyst aging rates of catalysts containing dehydrogenation/hydrogenation metals and a microporous crystalline material, increased after air regenerations or after high temperature calcination during catalyst preparation. It has been discovered that incorporation of a metal selected from the group consisting of iridium, ruthenium, and rhenium reduces that observed aging rate.

BACKGROUND OF THE INVENTION

Naturally occurring and synthetic crystalline microporous materials have been demonstrated to exhibit catalytic properties for various types of hydrocarbon conversions. The term "crystalline" used to refer to these materials relates to the ordered definite crystalline structure of the material which is unique and thus identifiable by a characteristic X-ray diffraction pattern.

The term "microporous" as it refers to such material relates to pores, or channels, with diameters of less than 20 Angstroms. Examples of these microporous crystalline materials include crystalline silicates, crystalline alumino-silicates (zeolites), crystalline ALPOs, crystalline SAPO and related compositions and intercalated pillared materials derived from clays, layered silicates and titanates. The crystalline silicate, alumino silicate (zeolites), ALPOs and SAPOs, have pores of uniform size and channel systems which are uniquely determined by unit structure of the material. The uniform pore size and/or channel systems allow such a material to selectively absorb molecules of certain dimensions and shapes. In the art, microporous material having pores, or channels, of less than 20 Angstroms, can be divided into small, medium and large pore by the diameters of those pores, or channels. The pores of the small pore material have an average diameter of less than 5 Angstroms; medium size pores range from an average diameter of about 5 to about 7 Angstroms, and large pore silicates indicates a diameter of greater than about 7. The word "average" is used to refer to diameter to embrace those species in which the pore is elliptical. Alternatively, the demarcation between small, medium, and large pore materials can be based on the following sorption properties (measured at room temperature for crystallites having a minimum dimension of 0.1 micron):

1. Small pore: n-$C_6$/i-$C_6$ sorption ratio greater than approximately 10.
2. Medium pore: n-$C_6$/i-$C_6$ is less than 10 and n-$C_6$/Mesitylene sorption ratio greater than approximately 5.
3. Large pore: n-$C_6$/Mesitylene sorption ratio less than approximately 5.

In the art, zeolites are a subclass of crystalline microporous silicates. Zeolites can contain aluminum as well as silicon. In some zeolites, the upper limit of the silicon/aluminum atomic ratio is unbounded. ZSM-5 is one such example wherein the silicon/aluminum atomic ratio is at least 2.5 and up to infinity. By way of illustration, U.S. Pat. No. 3,941,871, reissued as RE 29,948, discloses a porous crystalline silicate made from a reaction mixture containing no deliberately added aluminum and exhibiting the X-ray diffraction pattern characteristic of ZSM-5 zeolites; in certain examples tin is deliberately added to the silicate synthesis mixture.

Zeolites can be acidic or non-acidic, depending on the framework aluminum content and on the amount of compensating cations, such as $Na^+$, $K^+$, etc. ALPOs described in U.S. Pat. No. 4,310,440, which is incorporated by reference herein, are neutral. SAPOs described for example in U.S. Pat. No. 4,440,871, which is incorporated by reference herein, can be acidic or non-acidic depending on the ratio of framework Al:P therein and the compensating cation, such as $Na^+$, $K^+$ (other than proton species and other than proton forming species such as $NH^+_4$). ELAPOs are described in U.S. Pat. No. 4,500,651, while are described in U.S. Pat. Nos. 4,544,143 and 4,567,029, each of said latter three patents being incorporated by reference herein.

SUMMARY OF THE INVENTION

The present invention is directed to a new composition of matter, to its method of production and to its use as a catalyst in paraffin dehydrogenation and paraffin dehydrocyclization. The composition comprises rhenium, ruthenium or iridium and a support comprising a microporous crystalline material and platinum or palladium.

DESCRIPTION OF THE DRAWINGS

FIG. 1 is a graph plot of isobutane yield vs. reaction time.

FIG. 2 illustrates the aging behavior of iridium-Pt/Sn-ZSM-5 and is a plot of isobutane yield vs. hours on stream.

DETAILED DESCRIPTION OF THE INVENTION

The compositions of the invention contain 0.01 to 20 weight percent iridium, ruthenium or rhenium. Practically, that content will generally range from 0.1 to 10 weight percent.

The crystalline microporous materials can contain a modifier selected from the group consisting of tin, thallium indium and lead present in an amount which can range from 0.01 to 20 weight percent. Practically, the modifier content will range from 0.1 to 10 weight percent. Synthesis of the modifier containing microporous crystalline materials is described in U.S. Pat. Nos. 4,868,145, 4,931,416 and 4,886,926, each of which is relied upon and incorporated by reference herein.

The crystalline microporous materials of the invention are characterized by Si/Al ratios of at least 2 preferably at least 10. However, the silica:alumina ratio of the zeolite can be up to 1000, or greater. In a preferred embodiment the aluminum content of these materials is less than 0.1 weight percent and more preferably less than 0.02 weight percent.

The crystalline microporous material can contain additional other elements including boron, iron, chromium and gallium. The content of these other elements in the crystalline microporous can range from 0 to 10 weight percent.

The crystalline microporous materials of the invention, described herein, are crystalline in the sense that they are identifiable as isostructural with zeolites by X-ray powder diffraction pattern.

The crystalline microporous material has an X-ray diffraction pattern which corresponds to a zeolite, SAPO, ALPO, etc.

In a preferred embodiment the pore size of the microporous crystalline material (e.g., a silicate) ranges from about 5 to about 8 Angstroms. Preferably, the silicates exhibit X-ray diffraction patterns of zeolites which are characterized by Constraint Index of 1 to 12.

The method by which Constraint Index is determined is described fully in U.S. Pat. No. 4,016,218, incorporated herein by reference for details of the method. Constraint Index (CI) values for some typical zeolites including some which are suitable as catalysts in the process of this invention are:

| CI (at test temperature) | |
|---|---|
| ZSM-4 | 0.5 (316° C.) |
| ZSM-5 | 6–8.3 (371° C.–316° C.) |
| ZSM-11 | 5–8.7 (371° C.–316° C.) |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 1.5 (454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important and even critical definition of those zeolites which are useful in the process of the present invention. The very nature of this parameter and the above-referenced procedure by which it is determined, however, admits of the possibility that a given zeolite can be tested under somewhat different conditions and thereby exhibit different Constraint Indices. Constraint Index appears to vary somewhat with the severity of the conversion operation and the presence or absence of binder material. Similarly, other variables such as crystal size of the zeolite, the presence of occluded contaminants, etc., may affect the observed Constraint Index value. It will therefore be appreciated that it may be possible to select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites but that such are the cumulative result of several variables useful in the determination and calculation thereof. Thus, for a given zeolite exhibiting a CI value within the range of 5 or less, depending on the temperature employed during the test method within the range of 290° C. to about 538° C., with accompanying conversion between 10% and 60%, the CI may vary within the indicated range of 5 or less. Accordingly, it will be understood to those skilled in the art that the CI as utilized herein, while affording a highly useful means for characterizing the zeolites of interest, is approximately taking into consideration the manner of its determination including the possibility in some instances of compounding variable extremes. However, in all instances, at a temperature within the above-specified range of 290° C. to about 538° C., the CI will have a value for any given zeolite of interest herein of not greater than about 5 and preferably not greater than about 3. In a preferred embodiment the microporous crystalline material containing tin exhibits the structure of ZSM-5, by X-ray diffraction pattern. The X-ray diffraction pattern of ZSM-5 has been described in U.S. Pat. No. 3,702,886 and RE 29,948 each of which is incorporated by reference herein.

Another aspect of the invention is a catalyst comprising hydrogenation/dehydrogenation metal and the non-acidic crystalline microporous material. As catalysts these non-acidic forms of compositions exhibit extremely high selectivity for paraffin dehydrogenation and/or dehydrocyclization reactions, under conditions effective for paraffin dehydrogenation and/or aromatization.

The amount of dehydrogenation metal in the catalyst can range from 0.1 to 30 weight percent and preferably 0.01 to 10 weight percent of the crystalline microporous material. In a preferred embodiment, platinum is the hydrogenation/dehydrogenation metal. However, the hydrogenation/dehydrogenation metal can be any Group VIII metal including those of the platinum group, chromium and vanadium.

The compositions comprising hydrogenation/dehydrogenation metal combined with the crystalline do not exhibit any appreciable acid activity. These catalysts would meet the criteria of non-acidic catalysts described by Davis and Venuto, J. CATAL. Vol. 15, p.363 (1969). Thus, a non-equilibrium mixture of xylenes are formed from either n-octane or each individual methylheptane isomer, with the octane yielding more o-xylene and 2-methyl-heptane yielding mostly m-xylene, at conversions between 10 and 60%.

When, as in embodiments herein, the crystalline microporous dehydrogenation metal containing material exhibits an X-ray diffraction pattern of a zeolite, at least some of the dehydrogenation metal may be intrazeolitic, that is, some of that metal is within the pore structure of the crystal, although some of that metal can be on the surface of the crystal. A test for determining whether, for example, Pt is intrazeolitic or extrazeolitic in the case of ZSM-5 is reported by R. M. Dessau, J. CATAL. Vol. 89, p. 520 (1984). The test is based on the selective hydrogenation of olefins.

Compositions of the invention used in catalysis decrease the hydrogen content of the reactant to produce a product having the same number of carbon atoms as the number of carbon atoms in the reactant. By comparison modifier-free counterparts of those compositions catalyzed also hydrogenolysis of paraffins, e.g., to methane, as a major competing side reaction; and, accordingly, the latter compositions exhibit decreased selectivity for the aromatization of paraffins but increased selectivity for $C_1$–$C_5$ paraffin production.

Crystalline microporous materials containing 0.1 weight percent or less aluminum are the preferred embodiments of the examples. In materials of the invention, all cation-exchangeable sites are occupied by non-hydrogen (non-proton) and by non-hydrogen precursors, such as $NH_4^+$. Specifically, such sites are occupied by $Na^+$, $K^+$, $Cs^+$ or admixtures thereof. The alkali metals serve to neutralize any acidity due to framework aluminum. The source of alkali metal cation can derive from cations incorporated during synthesis, in excess of the aluminum content thereof. Alternatively, one can treat the final product with a basic solution of an alkali metal hydroxide as a final step prior to use, as described for example in U.S. Pat. No. 4,652,360.

In a preferred embodiment, the non-acidic crystalline microporous materials used in the invention are treated with $Pt(NH_3)_4Cl_2$ in aqueous solution which has a pH of at least about 7 to incorporate the necessary platinum for catalyst composition formulation. Iridium, ruthenium or rhenium can be added in the same way. Preferably, the iridium, ruthenium, or rhenium are deposited on the substrate, as e.g. salts, and then calcined in the presence of hydrogen to reduce the metal to elemental form.

The non-acidic, crystalline, microporous, material and dehydrogenation metal containing materials of the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. When used in dehydrogenation and/or dehydrocyclization, the material of the invention will preferably be combined with non-acidic matrix or binder materials. A preferred matrix or binder material would be silica, when the materials of the invention are used in dehydrogenation/hydrogenation or dehydrocyclization. In applications other than hydrogenation, dehydrogenation and/or dehydrocyclization, the matrix or binder material can be any of those including active and inactive material and synthetic or naturally occurring zeolites as well as inorganic materials such as clays, silica and/or metal oxides, e.g. alumina. The latter may be either naturally occurring or in the form of gelatinous precipitates or gels including mixtures of silica and metal oxides. Use of a material in conjunction with the new composition. i.e. combined therewith, which is active, tends to alter the conversion and/or selectivity of the overall catalyst in certain organic conversion processes. Inactive materials suitably serve as diluents to control the amount of conversion in a given process so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It may be desirable to provide a catalyst having good crush strength because in commercial use it is desirable to prevent the catalyst from breaking down into powder-like materials. These clay binders have been employed normally only for the purpose of improving the crush strength of the overall catalyst.

Naturally occurring clays which can be composited with the new crystal include the montmorillonite and kaolin families which include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also iclude inorganic oxides, notably alumina.

In addition to the foregoing materials, the crystalline material can be composited with a porous matrix material such as silica-alumina, silica-magnesia, silica-zirconia, silica-thoria, silica-beryllia, silica-titania we well as ternary compositions such as silica-alumina-thoria, silica-alumina-zirconia silica-alumina-magnesia and silica-magnesia-zirconia. The relative proportions of finely divided crystalline material and inorganic oxide gel matrix vary widely, with the crystal content ranging from about 1 to about 90 percent by weight and more usually, particularly when the composite is prepared in the form of beads, in the range of about 2 to about 80 weight percent of the composite.

These compositions of the invention exhibit high selectivity for dehydrogenation and/or dehydrocyclization and reforming, which is illustrated by the examples.

Catalytic Dehydrogenation and Dehydrocyclization

In accordance with the invention catalytic dehydrogenation comprises contacting an aliphatic, with the catalyst composition of the invention to produce the corresponding unsaturated analog together with at least one mole of $H_2$. The catalytic dehydrogenation exhibits high selectivity with respect to production of said unsaturated analog, with substantially little, if any, selectivity for hydrogenolysis (cracking) and with substantially little, if any, selectivity for isomerization.

In dehydrogenation the feedstocks comprise at least one unsubstituted or substituted straight or branched chain aliphatic compound in which the aliphatic moiety has two to five carbon atoms. In accordance with the invention, dehydrogenation of the aliphatic moiety occurs to yield the unsaturated analog. When the aliphatic moiety is substituted, the substituents can be aryls substituted or unsubstituted. The class of reactants includes alkanes of 2 to 5 carbon atoms including ethane, propane, butane, isobutane, pentane and 2-methylbutane. Dehydrogenation of those respective alkane reactants will yield ethylene, propylene, butene, isobutene, pentene and isopentene. Dehydrogenation of $C_6$ and $C_6+$ alkanes will produce aromatics.

The class of reactants includes olefins of 2 to 5 carbon atoms such as ethylene, butene, pentene, and isopentene. Dehydrogenation of $C_4+$ olefins will produce dienes. Dehydrogenation of ethylene will produce acetylene; dehydrogenation of butane will produce butadiene and dehydrogenation of isopentene will produce isoprene.

The class of reactants employed in the dehydrogenation of the invention includes aromatic substituted aliphatics, aryl substituted aliphatics. Preferably, the aliphatic group of the aryl substituted aliphatic contains less than four carbon atoms and more preferably more than 1 carbon atom. The aryl substituted aliphatic reactants embrace unsubstituted arylaliphatics and alkyl substituted aryl aliphatics and; similarly, each of the alkyls of said alkyl substituted alkylaryls contains preferably less than 4 carbon atoms. By way of illustration reactants such as ethyl benzene, diethylbenzene, ethyl toluene, and cumene are representative of these compounds. On dehydrogenation in accordance with the invention, ethyl benzene will produce styrene; ethyl toluene will produce p-methylstyrene; cumene, isopropenylbenzene; and diethylbenzene, divinylbenzene.

In accordance with the invention, catalytic dehydrogenation conditions include pressures varying from subatmospheric, to atmospheric to greater than atmospheric. Preferred pressures range from 0.1 atmospheres to atmospheric. However, pressures up to 500 psig can be employed. The dehydrogenation is conducted at elevated temperatures ranging from 400° C. to 700° C.

and most preferably from 300° C. to 600° C. Reactor inlet H₂/feed ratios are 5 or less; even at reactor inlet ratios of zero (0), there will be a hydrogen partial pressure in the reactor because hydrogen is a bi-product of dehydrogenation. The liquid hourly space velocity of 0.1 to 50, preferably 0.5 to 10.

Under these conditions, the catalytic dehydrogenation of the invention exhibits little if any selectivity for hydrogenolysis or for isomerization. Accordingly, the unsaturated product of the process of the invention can be characterized as substantially free of molecular products of less (fewer number) carbon atoms than the reactants and as substantially free of isomers of the reactant or of isomers of its unsaturated analogs of the reactant.

Dehydrogenation may be conducted in the presence or absence of purposefully added hydrogen and in the presence of diluents inert to conditions of the catalytic dehydrogenation such as nitrogen and methane. In particular, dehydrogenation can be advantageously conducted at low hydrogen pressure.

Dehydrocyclization in accordance with the invention comprises contacting an aliphatic of at least six (6) carbon atoms with the catalytic composition comprising a dehydrogenation/ hydrogenation metal which can be any Group VIII metal, preferably platinum.

When dehydrogenation, dehydrocyclization or reforming is undertaken over the catalyst in accordance with the invention, the temperature can range broadly from 800° F. to 1100° F., generally being greater than about 900° F., preferably being 900° F. (482° C.) to 1050° F.; the pressure will be from about 1 atmosphere to 500 psig, preferably from 30 psig to 250 psig; inlet H₂/hydrocarbon can be 5 or less, even zero (0) (because of hydrogen production during reforming, there will be a hydrogen partial pressure in the unit); while the LHSV (liquid hourly space velocity) can be 0.1 to 20, preferably 0.1 to 10.

EXAMPLES

EXAMPLE 1

A Pt/Sn-ZSM-5 catalyst, containing 0.43% Pt, 1.03% Sn, and 56 ppm Al, was prepared according to allowed U.S. application Ser. No. 211,198 filed Jun. 24, 1988, which is incorporated by reference herein, and then calcined first at 350° C. and then at 500° C. for one hour.

Iridium incorporation was achieved by impregnation of 3 grams of the above catalyst with 21 mg Na₂IrCl₆ to give 0.3 wt. % Ir on catalyst. After being dried in a vacuum oven, the catalyst was reduced in hydrogen during the usual reaction start-up procedure.

EXAMPLE 2

Isobutane dehydrogenation was undertaken. The activity and stability of the catalyst was evaluated at 554° C., 4.8 WHSV, and atmospheric pressure, in the absence of added hydrogen. Analyses were via on-line gas chromatography.

RESULTS AND DISCUSSION

The Pt/Sn-ZSM-5 catalyst calcined at 500° C. was impregnated with sodium hexachloroiridate, so as to produce a catalyst with 0.3 wt. % Ir.

The aging behavior of this iridium-containing Pt/Sn-ZSM-5 catalyst for isobutane dehydrogenation at 554° C., 4.8 WHSV, and atmospheric pressure, in the absence of added hydrogen, is shown in FIG. 1.

The presence of iridium clearly exerted a marked influence on the aging rate. Whereas the isobutene yield over the iridium-free catalyst dropped from 47 wt. % to 32% in 8 days, the iridium-containing catalyst yielded better than 45% isobutene during 15 days on stream, under identical reaction conditions (554° C.).

Isobutane dehydrogenation over the iridium-Pt/Sn-ZSM-5 catalyst was then continued for an additional 12 days at a slightly lower temperature of 538° C. During this span, the isobutene yield decreased only slightly, from 39% to 38% (FIG. 2).

What is claimed is:

1. A non-acidic catalyst comprising iridium supported on a non-acidic composition consisting of a dehydrogenation/hydrogenation metal and a non-acidic microporous crystalline material.

2. The catalyst of claim 1, wherein ruthenium, rhenium or iridium is present in an amount ranging from 0.1 to 10 weight percent.

3. The catalyst of claim 1, wherein the non-acidic microporous crystalline material contains an element selected from the group consisting of indium, tin thallium and lead in an amount which ranges from 0.1 to 20 weight percent.

4. The catalyst of claim 2, wherein the amount of dehydrogenation metal ranges from 0.1 to 20 weight percent.

5. The catalyst of claim 1, wherein the material exhibits an X-ray pattern corresponding to a zeolite.

6. The catalyst of claim 5, wherein the zeolite is characterized by a constraint index of 1 to 12.

7. The catalyst of claim 6, wherein the zeolite is ZSM-5, ZSM-11, ZSM-12, ZSM-22, ZSM-23, ZSM-48 and ZSM-50.

8. The catalyst of claim 1, wherein the dehydrogenation/hydrogenation metal is platinum.

9. The catalyst of claim 4, wherein the dehydrogenation/hydrogenation metal is platinum.

10. The catalyst of claim 5, wherein the zeolite is ZSM-5.

11. The catalyst of claim 10, wherein the material contains 0.1 to 10 weight percent tin.

12. The catalyst of claim 11, wherein the material contains less than 0.01 weight percent aluminum.

13. A non-acidic catalyst comprising from 0.1 to 20 weight percent iridium supported on a non-acidic composition consisting of platinum and a non-acidic microporous crystalline material which microporous crystalline material exhibits the X-ray diffraction pattern of zeolite selected from the group consisting of ZSM-5, ZSM-11, ZSM-12, ZSM-22, ZSM-23, ZSM-48 and ZSM-50, which microporous crystalline material contains less than 0.01 weight percent aluminum; which microporous crystalline material contains an element selected from the group consisting of indium, tin thallium and lead in an amount which ranges from 0.1 to 20 weight percent.

14. The catalyst of claim 13, wherein the zeolite is ZSM-5.

15. The catalyst of claim 13, wherein the material contains 0.1 to 10 weight percent tin.

16. A non-acidic catalyst comprising from 0.1 to 20 weight percent iridium supported on a non-acidic composition consisting of platinum and a non-acidic microporous crystalline material, which microporous crystalline material exhibits the X-ray diffraction pattern of ZSM-5, which microporous crystalline material contains less than 0.01 weight percent aluminum; which microporous crystalline material contains tin in an amount which ranges from 0.1 to 20 weight percent.

* * * * *